(12) United States Patent
Kimura et al.

(10) Patent No.: US 7,812,171 B2
(45) Date of Patent: Oct. 12, 2010

(54) BLACK PIGMENT, BLACK PIGMENT DISPERSION AND BLACK RESIN COMPOSITION COMPRISING THE SAME

(75) Inventors: Keizo Kimura, Kanagawa (JP); Osamu Uchida, Kanagawa (JP); Katsuyoshi Yamakawa, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 139 days.

(21) Appl. No.: 11/938,990

(22) Filed: Nov. 13, 2007

(65) Prior Publication Data

US 2008/0262237 A1  Oct. 23, 2008

(30) Foreign Application Priority Data

Nov. 17, 2006  (JP) .............................. 2006 311348

(51) Int. Cl.
*C07D 213/62* (2006.01)
(52) U.S. Cl. .................................................... 546/298
(58) Field of Classification Search ................. 546/298
See application file for complete search history.

(56) References Cited

U.S. PATENT DOCUMENTS

| | | | | |
|---|---|---|---|---|
| 5,437,970 A | * | 8/1995 | Shono | ........................ 430/522 |
| 6,787,295 B1 | * | 9/2004 | Nakanishi et al. | ............ 430/546 |
| 6,824,968 B2 | * | 11/2004 | Maeno et al. | ................ 430/505 |

FOREIGN PATENT DOCUMENTS

| | | | |
|---|---|---|---|
| EP | 577138 | * | 1/1994 |
| JP | 08015821 | * | 1/1996 |

* cited by examiner

*Primary Examiner*—D. Margaret Seaman
*Assistant Examiner*—Niloofar Rahmani
(74) *Attorney, Agent, or Firm*—Sughrue Mion, PLLC

(57) ABSTRACT

The present invention provides a black pigment consisting of an oxonol compound having a mean particle diameter ranging from 0.01 to 10.0 micrometers, and a black pigment dispersion and a black resin composition comprising the black pigment.

6 Claims, No Drawings

BLACK PIGMENT, BLACK PIGMENT DISPERSION AND BLACK RESIN COMPOSITION COMPRISING THE SAME

CROSS-REFERENCE TO RELATED APPLICATIONS

This application claims the benefit of priority under 35 USC 119 to Japanese Patent Application No. 2006-311348 filed on Nov. 17, 2006, which is expressly incorporated herein by reference in its entirety.

BACKGROUND OF THE INVENTION

1. Field of the Invention

The present invention relates to a black oxonol pigment, to a black pigment dispersion comprising the black oxonol pigment, and to a black resin composition comprising the black oxonol pigment. More particularly, the present invention relates to a black oxonol pigment with little absorption in the near infrared range, to a black pigment dispersion comprising the black oxonol pigment, and to a black resin composition comprising the black oxonol pigment.

2. Discussion of the Background

Conventionally, carbon black, aniline black, iron oxides and the like have been employed as black pigments. These pigments absorb light over a wide range spanning from the ultraviolet range to the far infrared range. In contrast, some semiconductor lasers, and sensors employing such lasers, use light in the near infrared range. There is a problem in that conventional black pigments cannot be differentiated from near infrared absorbing pigments by such sensors. When paint or plastic materials comprising conventional black pigments are employed on automobiles or buildings, there are problems in that the internal temperature rises, cooling efficiency decreases, and surfaces are denatured by heat.

To solve these problems, various pigments have been proposed as black pigments that do not absorb light in the near infrared range. As such pigments, azo pigments are described, for example, in Japanese Unexamined Patent Publication (KOKAI) Heisei No. 11-236,514, and Japanese Unexamined Patent Publication (KOKAI) No. 2002-256,165 or English language family member U.S. Patent Application Publication No. 2002/0121228 A1, which are expressly incorporated herein by reference in their entirety, and pigments such as perilene, diketopyrrolopyrrole, quinophthalone, perinone, dioxazine, phthalocyanine, isoindoline, and isoindolinone are described, for example, in Japanese Unexamined Patent Publication (KOKAI) No. 2002-20,647, Japanese Unexamined Patent Publication (KOKAI) No. 2002-60,698 or English language family member U.S. Patent Application Publication No. 2003/0030041 A1, and Japanese Unexamined Patent Publication (KOKAI) No. 2005-132,461, which are expressly incorporated herein by reference in their entirety. However, further improvement in hue, that is, increased blackness and better transparency in the near infrared range, is desirable in these pigments. Further, better pigment processing (comminution) properties and ease of pigment dispersion are also desirable.

SUMMARY OF THE INVENTION

An aspect of the present invention provides for a novel black pigment having high light transmittance in the near infrared range, exhibiting excellent hue, and lending itself readily to pigment processing and dispersion.

The present inventors conducted extensive research on how to achieve such a black pigment, focusing on the oxonol compounds employed for purposes such as antihalation in conventional silver halide color photography photosensitive materials. Oxonol compounds are materials that are readily processed into microparticles, and in a microparticulate state, exhibit good dispersion properties. However, in silver halide color photography photosensitive materials, oxonol compounds fade during the processing of the photosensitive materials, and thus do not function as pigments; that is, they do not play a role in exhibiting color in images or markings. That is, the use of oxonol compounds as black pigments has been completely unknown until now. Further, paints, plastic materials, films, toners for printing, and the like based on resin compositions employing oxonol compounds are also completely unknown. The present inventors conducted further research into achieving the above-stated black pigment by employing oxonol compounds as black pigments. As a result, they discovered that oxonol compounds having a prescribed mean particle diameter had high light transparency in the near infrared range and exhibited good hue; the present invention was devised on that basis.

An aspect of the present invention relates to a black pigment consisting of an oxonol compound having a mean particle diameter ranging from 0.01 to 10.0 micrometers.

The oxonol compound may be denoted by general formula (I).

General formula (I)

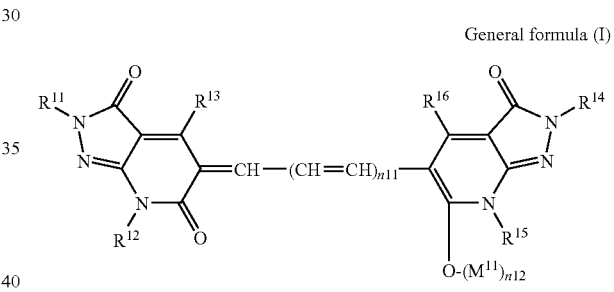

In general formula (I), $R^{11}$ and $R^{14}$ each independently denotes a hydrogen atom, aliphatic group, aromatic group, or a heterocyclic group bonded through a carbon atom; $R^{12}$ and $R^{15}$ each independently denotes a hydrogen atom, aliphatic group, aromatic group, heterocyclic group bonded through a carbon atom, $-COR^7$, or $-SO_2R^{17}$, $R^{17}$ denotes an aliphatic group, aromatic group, or heterocyclic group bonded through a carbon atom; $R^{13}$ and $R^{16}$ each independently denotes a hydrogen atom, aliphatic group, aromatic group, heterocyclic group, cyano group, $-CO_2R^{19}$, $-OR^{19}$, $-NR^{19}R^{20}$, $-N(R^{19})COR^{18}$, $-CONR^{18}R^{19}$, or $-N(R^{19})CONR^{20}R^{21}$, $R^{18}$ denotes an aliphatic group, aromatic group, or heterocyclic group bonded through a carbon atom, $R^{19}$, $R^{20}$, and $R^{21}$ each independently denote a hydrogen atom, aliphatic group, aromatic group, or heterocyclic group bonded through a carbon atom; n11 denotes 1 or 2; $M^{11}$ denotes a hydrogen ion or a cation with a valence ranging from 1 to 3; and n12 denotes an inverse number of the valence of $M^{11}$.

A further aspect of the present invention relates to a black pigment dispersion comprising the black pigment.

The black pigment dispersion may comprise the black pigment in an amount of 0.2 to 30 weight percent.

The black pigment dispersion may have a transmittance of light having a wavelength of 750 to 1,200 nm in a range of 60 to 100 percent.

A further aspect of the present invention relates to a black resin composition comprising the black pigment and a resin component.

The black resin composition may comprises said black pigment in an amount of 0.2 to 40 weight percent.

The black resin composition may have a transmittance of light having a wavelength of 750 to 1,200 nm in a range of 60 to 100 percent.

The present invention can provide a novel black pigment that absorbs little near infrared light and that is suited to use in marking materials, paints, plastic materials, and the like, a liquid dispersion comprising the black pigment, and a resin composition comprising the black pigment.

Other exemplary embodiments and advantages of the present invention may be ascertained by reviewing the present disclosure.

DESCRIPTIONS OF THE EMBODIMENTS

The following preferred specific embodiments are, therefore, to be construed as merely illustrative, and non-limiting to the remainder of the disclosure in any way whatsoever. In this regard, no attempt is made to show structural details of the present invention in more detail than is necessary for fundamental understanding of the present invention; the description taken with the drawings making apparent to those skilled in the art how several forms of the present invention may be embodied in practice.

In the present invention, various known methods may be employed to measure the mean particle diameter. The use of an optical method such as light scattering is desirable.

A common spectral absorption measuring device (for example, a U-4100 Spectrophotometer made by Hitachi High Technologies (Ltd.)) may be employed to measure spectral absorption in the present invention.

In the present invention, the term "aliphatic group" means an alkyl group, substituted alkyl group, alkenyl group, substituted alkenyl group, alkynyl group, substituted alkynyl group, aralkyl group, or substituted aralkyl group. The alkyl group may be branched or cyclic. The number of carbon atoms on the alkyl group is preferably 1 to 20, more preferably 1 to 18. Details of the alkyl moiety on a substituted alkyl group are the same as those described above for the alkyl group. The alkenyl group may be branched or cyclic. The number of carbon atoms on the alkenyl group is preferably 2 to 20, more preferably 2 to 18. Details of the alkenyl moiety of a substituted alkenyl group are the same as those described above for the alkenyl group. The alkynyl group may be branched or cyclic. The number of carbon atoms on the alkynyl group is preferably 2 to 20, more preferably 2 to 18. Details of the alkynyl moiety of a substituted alkynyl group are the same as those described above for the alkynyl group. Details of the alkyl moiety of an aralkyl group or substituted aralkyl group are the same as those described above for the alkyl group. Details of the aryl moiety of an aralkyl group or substituted aralkyl group are the same as those described below for the aryl group.

Examples of substituents on the alkyl moiety of a substituted alkyl group, substituted alkenyl group, substituted alkynyl group, or substituted aralkyl group are: halogen atoms (such as chlorine atoms, bromine atoms, and iodine atoms); alkyl groups (denoting straight chain, branched, or cyclic substituted or unsubstituted alkyl groups, including alkyl groups (preferably alkyl groups having 1 to 30 carbon atoms, such as methyl groups, ethyl groups, n-propyl groups, isopropyl groups, t-butyl groups, n-octyl groups, eicosyl groups, 2-chloroethyl groups, 2-cyanoethyl groups, and 2-ethylhexyl groups), cycloalkyl groups (preferably substituted or unsubstituted cycloalkyl groups having 3 to 30 carbon atoms, such as cyclohexyl groups, cyclopentyl groups, and 4-n-dodecylcyclohexyl groups), bicycloalkyl groups (preferably substituted or unsubstituted bicycloalkyl groups having 5 to 30 carbon atoms, that is, monovalent groups in which one of the hydrogen atoms has been removed from a bicycloalkane having 5 to 30 carbon atoms, such as bicyclo[1,2,2]heptane-2-yl, bicyclo[2,2,2]octane-3-yl), and tricyclo structures having multiple cyclic structures; in the description given below, the alkyl group in a substituent (such as the alkyl group in an alkylthio group) also denotes such an alkyl group); alkenyl groups (denoting straight chain, branched, or cyclic substituted or unsubstituted alkenyl groups including alkenyl groups (such as vinyl groups, allyl groups, prenyl groups, geranyl groups, and oleyl groups), cycloalkenyl groups (preferably substituted or unsubstituted cycloalkenyl groups having 3 to 30 carbon atoms, that is, monovalent groups in which one of the hydrogen atoms has been removed from a cycloalkene having 3 to 30 carbon atoms, such as 2-cyclopentene-1-yl and 2-cyclohexene-1-yl), bicycloalkenyl groups (including substituted and unsubstituted bicycloalkenyl groups, preferably substituted or unsubstituted bicycloalkenyl groups having 5 to 30 carbon atoms, that is, monovalent groups in which one of the hydrogen atoms in a bicycloalkene having one double bond has been removed, such as bicyclo[2,2,1]hepto-2-en-1-yl and bicyclo[2,2,2]octo-2-en-4-yl)); alkynyl groups (preferably substituted or unsubstituted alkynyl groups having 2 to 30 carbon atoms such as ethynyl groups, propargyl groups, and trimethylsilylethynyl groups); aryl groups (preferably substituted or unsubstituted aryl groups having 6 to 30 carbon atoms such as phenyl groups, p-tolyl groups, naphthyl groups, m-chlorophenyl groups, and o-hexadecanoylaminophenyl groups); heterocyclic groups (preferably five or six-membered, substituted or unsubstituted monovalent groups in which a hydrogen atom has been removed from an aromatic or nonaromatic heterocyclic compound, more preferably five or six-membered aromatic heterocyclic groups having 3 to 30 carbon atoms, such as 1-pyrazolyl groups, 2-furyl groups, 2-thienyl groups, 2-pyrimidinyl groups, and 2-benzothiazolyl groups); cyano groups; hydroxyl groups; nitro groups; carboxyl groups; alkoxy groups (preferably substituted or unsubstituted alkoxy groups having 1 to 30 carbon atoms such as methoxy groups, ethoxy groups, isopropoxy groups, t-butoxy groups, n-octyloxy groups, and 2-methoxyethoxy groups); aryloxy groups (preferably substituted or unsubstituted aryloxy groups having 6 to 30 carbon atoms such as phenoxy groups, 2-methylphenoxy groups, 4-t-butylphenoxy groups, 3-nitrophenoxy groups, 2-tetradecanoylaminophenoxy groups); silyloxy groups (preferably silyloxy groups having 3 to 20 carbon atoms such as trimethylsilyloxy groups and t-butyldimethylsilyloxy groups); heterocyclooxy groups (preferably substituted or unsubstituted heterocyclooxy groups having 2 to 30 carbon atoms such as 1-phenyltetrazole-5-oxy groups and 2-tetrahydropyranyloxy groups); acyloxy groups (preferably formyloxy groups, substituted or unsubstituted alkylcarbonyloxy groups having 2 to 30 carbon atoms, and substituted or unsubstituted arylcarbonyloxy groups having 6 to 30 carbon atoms, such as formyloxy groups, acetyloxy groups, pivaloyloxy groups, stearoyloxy groups, benzoyloxy groups, and p-methoxyphenylcarbonyloxy groups); carbamoyloxy groups (preferably substituted or unsubstituted carbamoyloxy groups having 1 to 30 carbon atoms such as N,N-dimethylcarbamoyloxy groups, N,N-diethylcarbamoyloxy groups, morpholinocarbonyloxy groups, N,N-di-n-octylaminocarbonyloxy groups, and N-n-octylcarbamoyloxy groups);

alkoxycarbonyloxy groups (preferably substituted or unsubstituted alkoxycarbonyloxy groups having 2 to 30 carbon atoms such as methoxycarbonyloxy groups, ethoxycarbonyloxy groups, t-butoxycarbonyloxy groups, and n-octylcarbonyloxy groups); aryloxycarbonyloxy groups (preferably substituted or unsubstituted aryloxycarbonyloxy groups having 7 to 30 carbon atoms such as phenoxycarbonyloxy groups, p-methoxyphenoxycarbonyloxy groups, and p-n-hexadecyloxyphenoxycarbonyloxy groups); amino groups (preferably amino groups, substituted or unsubstituted alkylamino groups having 1 to 30 carbon atoms and substituted or unsubstituted anilino groups having 6 to 30 carbon atoms such as amino groups, methylamino groups, dimethylamino groups, anilino groups, N-methylanilino groups, and diphenylamino groups); acylamino groups (preferably formylamino groups, substituted or unsubstituted alkylcarbonylamino groups having 1 to 30 carbon atoms, and substituted or unsubstituted arylcarbonylamino groups having 6 to 30 carbon atoms such as formylamino groups, acetylamino groups, pivaloylamino groups, lauroylamino groups, benzoylamino groups, and 3,4,5-tri-n-octyloxyphenylcarbonylamino groups); aminocarbonylamino groups (preferably substituted or unsubstituted aminocarbonylamino groups having 1 to 30 carbon atoms such as carbamoylamino groups, N,N-dimethylaminocarbonylamino groups, N,N-diethylaminocarbonylamino groups, and morpholinocarbonylamino groups); alkoxycarbonylamino groups (preferably substituted or unsubstituted alkoxycarbonylamino groups having 2 to 30 carbon atoms such as methoxycarbonylamino groups, ethoxycarbonylamino groups, t-butoxycarbonylamino groups, n-octadecyloxycarbonylamino groups, and N-methyl-methoxycarbonylamino groups); aryloxycarbonylamino groups (preferably substituted or unsubstituted aryloxycarbonylamino groups having 7 to 30 carbon atoms such as phenoxycarbonylamino groups, p-chlorophenoxycarbonylamino groups, and m-n-octyloxyphenoxycarbonylamino groups); sulfamoylamino groups (preferably substituted or unsubstituted sulfamoylamino groups having 0 to 30 carbon atoms, such as sulfamoylamino groups, N,N-dimethylaminosulfonylamino groups, and N-n-octylaminosulfonylamino groups); alkyl and arylsulfonylamino groups (preferably substituted or unsubstituted alkylsulfonylamino groups having 1 to 30 carbon atoms and substituted or unsubstituted arylsulfonylamino groups having 6 to 30 carbon atoms, such as methylsulfonylamino groups, butylsulfonylamino groups, phenylsulfonylamino groups, 2,3,5-trichlorophenylsulfonylamino groups, and p-methylphenylsulfonylamino groups); mercapto groups; alkylthio groups (preferably substituted or unsubstituted alkylthio groups having 1 to 30 carbon atoms, such as methylthio groups, ethylthio groups, and n-hexadecylthio groups); arylthio groups (preferably substituted or unsubstituted arylthio groups having 6 to 30 carbon atoms, such as phenylthio groups, p-chlorophenylthio groups, and m-methoxyphenylthio groups); heterocyclothio groups (preferably substituted or unsubstituted heterocyclothio groups having 2 to 30 carbon atoms, such as 2-benzothiazolylthio groups and 1-phenyltetrazole-5-ylthio groups); sulfamoyl groups (preferably substituted or unsubstituted sulfamoyl groups having 0 to 30 carbon atoms, such as N-ethylsulfamoyl groups, N-(3-dodecyloxypropyl)sulfamoyl groups, N,N-dimethylsulfamoyl groups, N-acetylsulfamoyl groups, N-benzoylsulfamoyl groups, and N—(N'-phenylcarbamoyl)sulfamoyl groups); sulfo groups; alkyl and arylsulfinyl groups (preferably substituted or unsubstituted alkylsulfinyl groups having 1 to 30 carbon atoms or substituted or unsubstituted arylsulfinyl groups having 6 to 30 carbon atoms, such as methylsulfinyl groups, ethylsulfinyl groups, phenylsulfinyl groups, and p-methylphenylsulfinyl groups); alkyl and aryl sulfonyl groups (preferably substituted or unsubstituted alkylsulfonyl groups having 1 to 30 carbon atoms or substituted or unsubstituted arylsulfonyl groups having 6 to 30 carbon atoms, such as methylsulfonyl groups, ethylsulfonyl groups, phenyl sulfonyl groups, and p-methylphenylsulfonyl groups); acyl groups (preferably formyl groups, substituted or unsubstituted alkylcarbonyl groups having 2 to 30 carbon atoms, substituted or unsubstituted arylcarbonyl groups having 7 to 30 carbon atoms, or substituted or unsubstituted heterocyclocarbonyl groups bonded through a carbon atom to the carbonyl group and having 4 to 30 carbon atoms, such as acetyl groups, pivaloyl groups, 2-chloroacetyl groups, stearoyl groups, benzoyl groups, p-n-octyloxyphenylcarbonyl groups, 2-pyridylcarbonyl groups, and 2-furylcarbonyl groups); aryloxycarbonyl groups (preferably substituted or unsubstituted aryloxycarbonyl groups having 7 to 30 carbon atoms, such as phenoxycarbonyl groups, o-chlorophenoxycarbonyl groups, m-nitrophenoxycarbonyl groups, and p-t-butylphenoxycarbonyl groups); alkoxycarbonyl groups (preferably substituted or unsubstituted alkoxycarbonyl groups having 2 to 30 carbon atoms, such as methoxycarbonyl groups, ethoxycarbonyl groups, t-butoxycarbonyl groups, and n-octadecyloxycarbonyl groups); carbamoyl groups (preferably substituted or unsubstituted carbamoyl groups having 1 to 30 carbon atoms, such as carbamoyl groups, N-methylcarbamoyl groups, N,N-dimethylcarbamoyl groups, N,N-di-n-octylcarbamoyl groups, and N-(methylsulfonyl)carbamoyl groups); aryl and heterocycloazo groups (preferably substituted or unsubstituted arylazo groups having 6 to 30 carbon atoms or substituted or unsubstituted heterocycloazo groups having 3 to 30 carbon atoms, such as phenylazo groups, p-chlorophenylazo groups, 5-ethylthio-1,3,4-thiadiazole-2-ylazo groups); imido groups (preferably N-succinimide groups and N-phthalimide); phosphino groups (preferably substituted or unsubstituted phosphino groups having 2 to 30 carbon atoms, such as dimethylphosphino groups, diphenylphosphino groups, and methylphenoxyphosphino groups); phosphinyl groups (preferably substituted or unsubstituted phosphinyl groups having 2 to 30 carbon atoms, such as phosphinyl groups, dioctyloxyphosphinyl groups, and diethoxyphosphinyl groups); phosphinyloxy groups (preferably substituted or unsubstituted phosphinyloxy groups having 2 to 30 carbon atoms, such as diphenoxyphosphinyloxy groups and dioctyloxyphosphinyloxy groups); phosphinylamino groups (preferably substituted or unsubstituted phosphinoamino groups having 2 to 30 carbon atoms, such as dimethoxyphosphinylamino groups and dimethylaminophosphinylamino groups); and silyl groups (preferably substituted or unsubstituted silyl groups having 3 to 30 carbon atoms, such as trimethylsilyl groups, t-butyldimethylsilyl groups, and phenyldimethylsilyl groups).

In those of the above functional groups that contain hydrogen atoms, the hydrogen atoms may be removed and replaced with the above-listed groups. Examples of such functional groups are alkylcarbonylaminosulfonyl groups, arylcarbonylaminosulfonyl groups, alkylsulfonylaminocarbonyl groups, and arylsulfonylaminocarbonyl groups. Examples thereof are methylsulfonylaminocarbonyl groups, p-methylphenylsulfonylaminocarbonyl groups, acetylaminosulfonyl groups, and benzoylaminosulfonyl groups.

Examples of substituents on the aryl moieties of substituted aralkyl groups are the same as those of the substituents for the substituted aryl groups given below.

In the present invention, the term "aromatic group" means an aryl group or substituted aryl group. An aromatic group may contain a condensed aliphatic ring, other aromatic ring, or hetero ring. The number of carbon atoms per aromatic group is preferably 6 to 40, more preferably 6 to 30, and further preferably, 6 to 20. Among them, a phenyl group and naphthyl group are desirable as the aryl group, with a phenyl group being particularly preferred.

Details of the aryl moiety of a substituted aryl group are the same as those described above for the aryl group. Examples of the substituents on substituted aryl groups are the same as the examples of substituents on the alkyl moieties of the above substituted alkyl groups, substituted alkenyl groups, substituted alkynyl groups, and substituted aralkyl groups.

In the present invention, the term "heterocyclic group" desirably includes five and six-membered saturated and unsaturated hetero rings. An aliphatic ring, aromatic ring, or another hetero ring may be condensed on the hetero ring. Examples of hetero atoms on the hetero ring are B, N, O, S, Se, and Te. N, O, and S are preferred as hetero atoms. In the hetero ring, a carbon atom desirably has free valence (single valence), that is, the heterocyclic group is desirably bonded at a carbon atom. The heterocyclic group preferably has 1 to 40, more preferably 1 to 30, and further preferably, 1 to 20 carbon atoms. Examples of saturated hetero rings are pyrrolidine rings, morpholino rings, 2-bora-1,3-dioxolan rings, and 1,3-thiazolidine rings. Examples of unsaturated hetero rings are imidazole rings, thiazole rings, benzothiazole rings, benzooxazole rings, benzotriazole rings, benzoselenazole rings, pyridine rings, pyrimidine rings, and quinoline rings. The heterocyclic group may comprise one or more substituents. Examples of such substituents are the same as the examples given for the substituents of the alkyl moiety in the substituted alkyl group, substituted alkenyl group, substituted alkynyl group, and substituted aralkyl group above.

[Black Pigment]

The black pigment of the present invention consists of an oxonol compound having a mean particle diameter ranging from 0.01 to 10.0 micrometers. Oxonol compounds are readily processed into microparticles and exhibit good dispersion properties; they are thus suitable for use as pigments. However, oxonol compounds that have a mean particle diameter of less than 0.01 micrometer tend to aggregate, do not readily disperse, and afford poor fastness. Thus, they are not suited to use as pigments. Additionally, when the mean particle diameter exceeds 10.0 micrometers, the transmittance of light in the near infrared region drops sharply and the degree of blackness in the visible light range also decreases. Thus, it becomes difficult to achieve the object of the present invention. By contrast, in oxonol compounds having the above-stated mean particle diameter, transmittance of light in the near infrared range and the degree of blackness in the visible light range are both high, rendering such compounds suitable for use as black pigments in applications in which near infrared radiation-absorbing pigments and black pigments should be differentiated. Since there is little absorption of light in the near infrared range, there is no increase in temperature with direct exposure to sunlight, rendering such compounds suited to applications requiring the passing of heat. The above mean particle diameter is preferably 0.01 to 5 micrometers, more preferably 0.02 to 2 micrometers, still more preferably 0.05 to 1 micrometer, and most preferably, 0.1 to 0.6 micrometer. The above mean particular diameter can be measured by known methods, but measurement by an optical method such as light scattering is desirable.

Various compounds having an oxonol skeleton are examples of the above oxonol compound. Of these, the oxonol compound denoted by general formula (I) below is a desirable example, as viewed from the various above-stated perspectives.

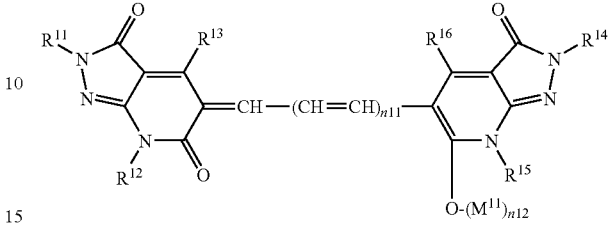

General formula (I)

The compound denoted by general formula (I) will be described below.

In general formula (I), $R^{11}$ to $R^{16}$, which will be described further below, may each be further substituted. When the substituent is a dissociative group, it comprises a cationic component in the form of a hydrogen atom or metal cation such as sodium, potassium, calcium, magnesium, or aluminum, or a nonmetal cation such as ammonium, tetramethylammonium, and tetraethylammonium. Of these, hydrogen atoms and metal cations are desirable, with hydrogen atoms and cations of groups IA, IIA, and IIIA of the Periodic Table of the Elements being preferred. Hydrogen atoms, lithium, sodium, potassium, rubidium, cesium, magnesium, calcium, strontium, barium, and aluminum are of even greater preference, with hydrogen atoms, magnesium, calcium, and barium being of still greater preference.

$R^{11}$ and $R^{14}$ each independently denotes a hydrogen atom, aliphatic group, aromatic group, or heterocyclic group bonded through a carbon atom. $R^{11}$ and $R^{14}$ preferably denote hydrogen atoms, aliphatic groups having 1 to 20 carbon atoms, aromatic groups having 6 to 20 carbon atoms, or heterocyclic groups bonded through carbon atoms and having 2 to 20 carbon atoms; more preferably denote hydrogen atoms, aliphatic groups having 1 to 10 carbon atoms, aromatic groups having 6 to 12 carbon atoms, or heterocyclic groups bonded through carbon atoms and having 2 to 10 carbon atoms; further preferably denote hydrogen atoms, alkyl groups having 1 to 10 carbon atoms, alkenyl groups, phenyl groups having 6 to 12 carbon atoms, naphthyl groups, or pyridyl groups having 5 to 10 carbon atoms; still more preferably denote hydrogen atoms, alkyl groups having 1 to 5 carbon atoms, or phenyl groups having 6 to 9 carbon atoms; still more preferably denote hydrogen atoms, alkyl groups having 1 to 2 carbon atoms, or phenyl groups having 6 to 8 carbon atoms; still more preferably denote hydrogen atoms, methyl groups, phenyl groups, 4-carboxyphenyl groups, 3-carboxyphenyl groups, and 3,5-dicarboxyphenyl groups; and most preferably denote 4-carboxyphenyl or 3,5-dicarboxyphenyl.

$R^{12}$ and $R^{15}$ each independently denotes a hydrogen atom, aliphatic group, aromatic group, or heterocyclic group bonded through a carbon atom, —$COR^7$, or —$SO_2R^{17}$. $R^{17}$ denotes an aliphatic group, aromatic group, or heterocyclic group bonded through a carbon atom.

$R^{12}$ and $R^{15}$ preferably denote hydrogen atoms, aliphatic groups having 1 to 20 carbon atoms, aromatic groups having 6 to 20 carbon atoms, or heterocyclic groups bonded through carbon atoms and having 2 to 20 carbon atoms; more preferably denote hydrogen atoms, aliphatic groups having 1 to 10 carbon atoms, aromatic groups having 6 to 12 carbon atoms, or heterocyclic groups bonded through carbon atoms and having 2 to 10 carbon atoms; further preferably denote hydrogen atoms, alkyl groups having 1 to 10 carbon atoms, alkenyl groups, phenyl groups having 6 to 12 carbon atoms, naphthyl groups, or pyridyl groups having 5 to 10 carbon atoms; even more preferably denote hydrogen atoms, alkyl groups having 1 to 4 carbon atoms, or phenyl groups having 6 to 10 carbon atoms; still more preferably denote hydrogen atoms, 3-hydroxypropane-1-yl groups, 2-hydroxyethyl groups, 2,3-dihydroxypropane-1-yl groups, phenyl groups, 4-carboxyphenyl groups, 3-carboxyphenyl groups, or 3,5-dicarboxyphenyl groups; and most preferably denote hydrogen atoms, 2-hydroxyethyl groups, 4-carboxyphenyl groups, 3-carboxyphenyl groups, or 3,5-dicarboxyphenyl groups.

$R^{13}$ and $R^{16}$ each independently denotes a hydrogen atom, aliphatic group, aromatic group, heterocyclic group, cyano group, $—CO_2R^{19}$, $—OR^{19}$, $—NR^{19}R^{20}$, $—N(R^{19})COR^{18}$, $—CONR^{18}R^{19}$, or $—N(R^{19})CONR^{20}R^{21}$. $R^{18}$ denotes an aliphatic group, an aromatic group, or a heterocyclic group bonded through a carbon atom. $R^{19}$, $R^{20}$, and $R^{21}$ each independently denotes a hydrogen atom, aliphatic group, aromatic group, or heterocyclic group bonded through a carbon atom.

$R^{13}$ and $R^{16}$ preferably denote hydrogen atoms, aliphatic groups having 1 to 20 carbon atoms, aromatic groups having 6 to 20 carbon atoms, heterocyclic groups having 2 to 20 carbon atoms, cyano groups, $—CO_2R^{19}$, $—OR^{19}$, $—NR^{19}R^{20}$, $—N(R^{19})COR^{18}$, $—CONR^{18}R^{19}$, or $—N(R^{19})CONR^{20}R^{21}$, in which case, $R^{18}$ denotes an aliphatic group having 1 to 20 carbon atoms, an aromatic group having 6 to 20 carbon atoms, or a heterocyclic group bonded through a carbon atom and having 2 to 20 carbon atoms, and $R^{19}$, $R^{20}$, and $R^{21}$ denote hydrogen atoms, aliphatic groups having 1 to 20 carbon atoms, aromatic groups having 6 to 20 carbon atoms, or heterocyclic groups bonded through carbon atoms and having 2 to 20 carbon atoms. $R^{13}$ and $R^{16}$ more preferably denote hydrogen atoms, aliphatic groups having 1 to 10 carbon atoms, aromatic groups having 6 to 12 carbon atoms, heterocyclic groups having 2 to 10 carbon atoms, cyano groups, $—CO_2R^9$, $—OR^{19}$, $—NR^{19}R^{20}$, $—N(R^{19})COR^{18}$, $—CONR^{18}R^{19}$, or $—N(R^{19})CONR^{20}R^{21}$; in which case $R^{18}$ denotes an aliphatic group having 1 to 10 carbon atoms, an aromatic group having 6 to 12 carbon atoms, or a heterocyclic group bonded through a carbon atom and having 2 to 10 carbon atoms, and $R^{19}$, $R^{20}$, and $R^{21}$ denote hydrogen atoms, aliphatic groups having 1 to 10 carbon atoms, aromatic groups having 6 to 12 carbon atoms, or heterocyclic groups bonded through carbon atoms and having 2 to 10 carbon atoms. $R^{13}$ and $R^{16}$ further preferably denote hydrogen atoms, alkenyl groups or alkyl groups having 1 to 10 carbon atoms, naphthyl groups or phenyl groups having 6 to 12 carbon atoms, pyridyl groups having 5 to 10 carbon atoms, cyano groups, $—CO_2R^{19}$, $—OR^{19}$, $—NR^{19}R^{20}$, $—N(R^{19})COR^8$, $—CONR^{18}R^{19}$, or $—N(R^{19})CONR^{20}R^{21}$; in which case $R^{18}$ denotes an aliphatic group having 1 to 10 carbon atoms, an aromatic group having 6 to 12 carbon atoms, or a heterocyclic group bonded through a carbon atom and having 2 to 10 carbon atoms, and $R^{19}$, $R^{20}$, and $R^{21}$ denote hydrogen atoms, alkenyl groups or alkyl groups having 1 to 10 carbon atoms, naphthyl groups or phenyl groups having 6 to 12 carbon atoms, or pyridyl groups having 5 to 10 carbon atoms. $R^{13}$ and $R^{16}$ still more preferably denote alkyl groups having 1 to 4 carbon atoms, phenyl groups having 6 to 9 carbon atoms, cyano groups, $—CO_2R^{19}$, $—OR^{19}$, $—NR^{19}R^{20}$, $—N(R^{19})COR^{18}$, $—CONR^{18}R^{19}$, or $—N(R^{19})CONR^{20}R^{21}$; in which case $R^{18}$ denotes an alkyl group having 1 to 4 carbon atoms, a phenyl group having 6 to 12 carbon atoms, or a pyridyl group having 5 to 10 carbon atoms, and $R^{19}$, $R^{20}$, and $R^{21}$ denote hydrogen atoms, alkyl groups having 1 to 3 carbon atoms, or phenyl groups having 6 to 9 carbon atoms. $R^{13}$ and $R^{16}$ still more preferably denote alkyl groups having 1 to 4 carbon atoms, phenyl groups having 6 to 7 carbon atoms, cyano groups, $—CO_2R^{19}$, $—OR^{19}$, $—N(R^{19})COR^{18}$, or $—CONR^{18}R^{19}$; in which case $R^{18}$ denotes an alkyl group having 1 to 2 carbon atoms or a phenyl group having 6 to 7 carbon atoms, and $R^{19}$ denotes a hydrogen atom, alkyl group having 1 to 2 carbon atoms, or a phenyl group having 6 to 7 carbon atoms. $R^{13}$ and $R^{16}$ most preferably denote hydrogen atoms, methyl groups, phenyl groups, cyano groups, methoxycarbonyl groups, ethoxycarbonyl groups, methoxy groups, ethoxy groups, acylamino groups, or benzoylamino groups.

n11 denotes 1 or 2, preferably 1.

$M^{11}$ denotes a hydrogen ion or a cation with a valence of 1 to 3. Examples of this cation are metal cations such as sodium, potassium, calcium, magnesium, and aluminum, and nonmetal ions such as ammonium, tetramethylammonium, and tetraethylammonium. $M^{11}$ desirably denotes a hydrogen ion or a metal ion; preferably a hydrogen ion or a cation from groups IA, IIA, or IIIA of the Periodic Table of the Elements; more preferably a hydrogen ion or lithium, sodium, potassium, rubidium, cesium, magnesium, calcium, strontium, barium, or aluminum; and still more preferably, a hydrogen ion, magnesium, calcium, or barium. n12 denotes an inverse number of the valence of $M^{11}$ Specific examples of the compound denoted by general formula (I) above will be given below. However, the present invention is not limited to the specific examples given below.

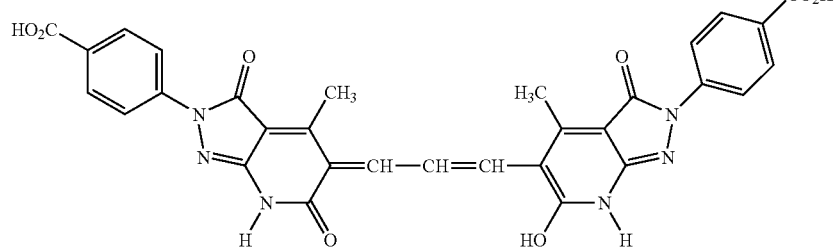

(I-1)

-continued
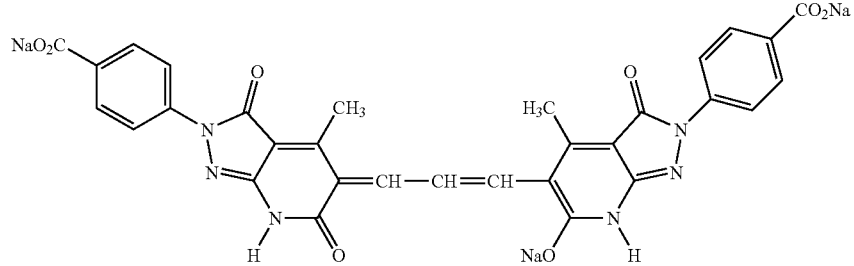
(I-2)
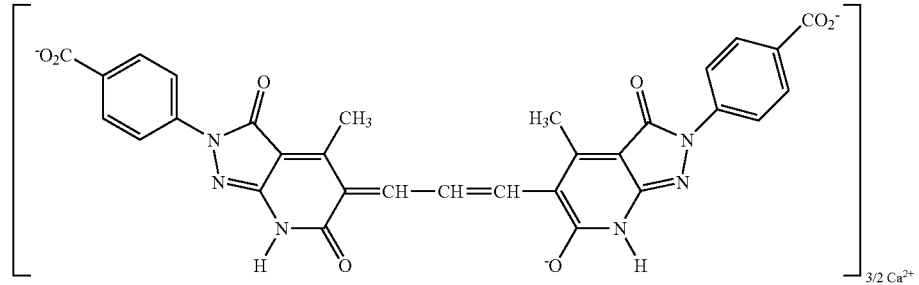
(I-3)
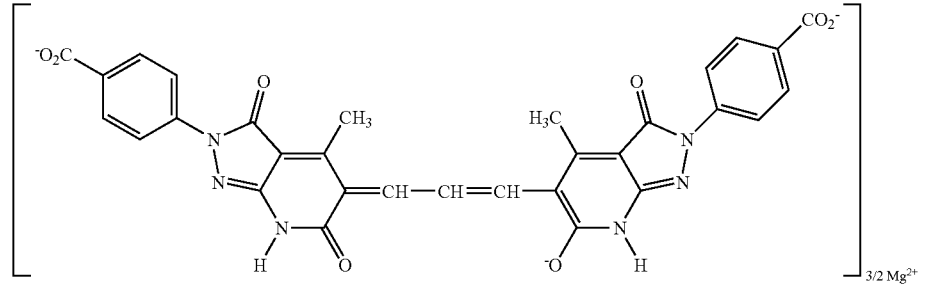
(I-4)
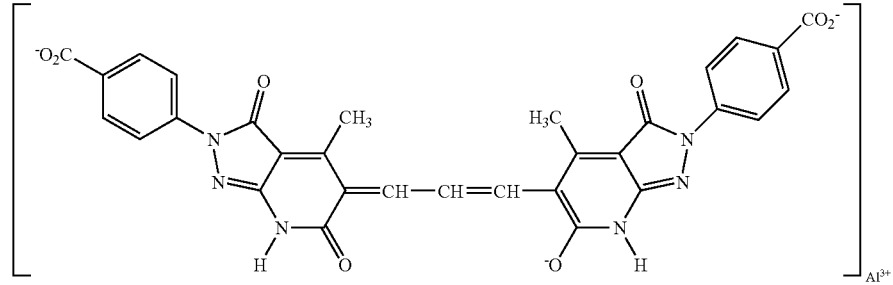
(I-5)
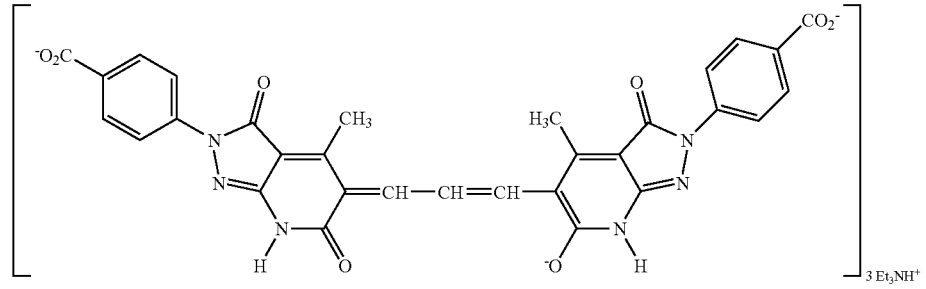
(I-6)

-continued
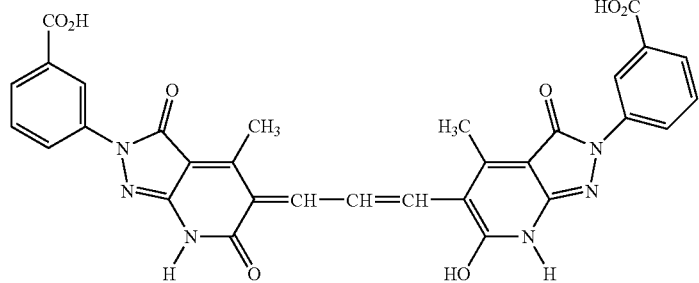
(I-7)
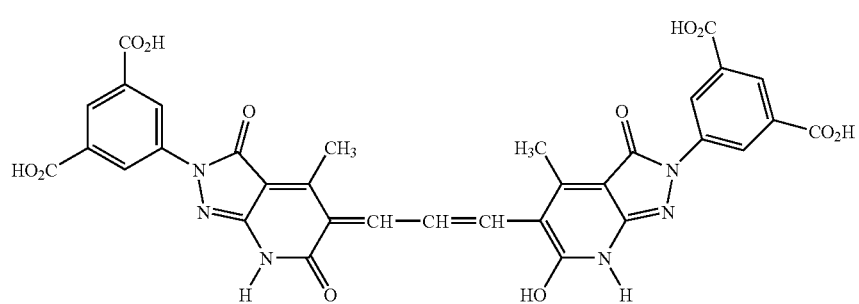
(I-8)
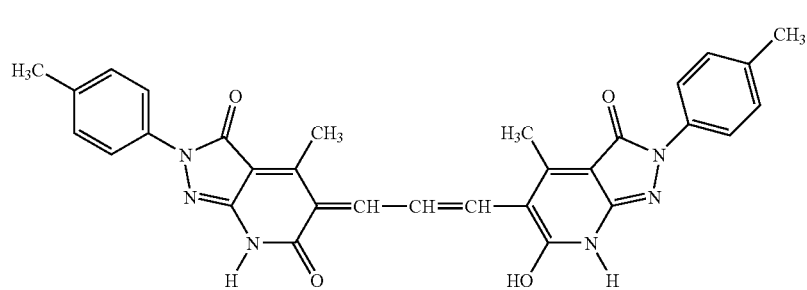
(I-9)
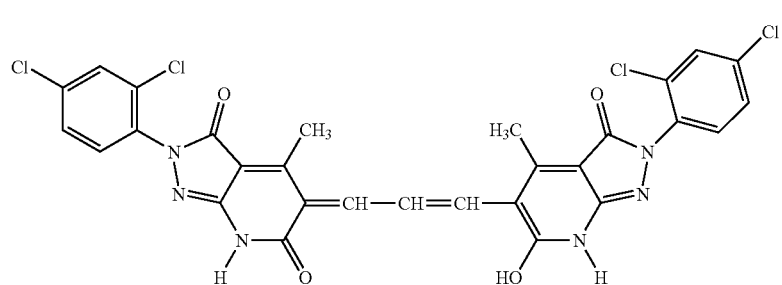
(I-10)
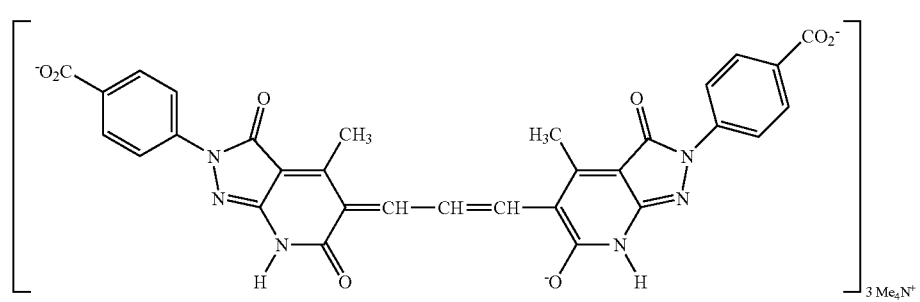
(I-11)

-continued
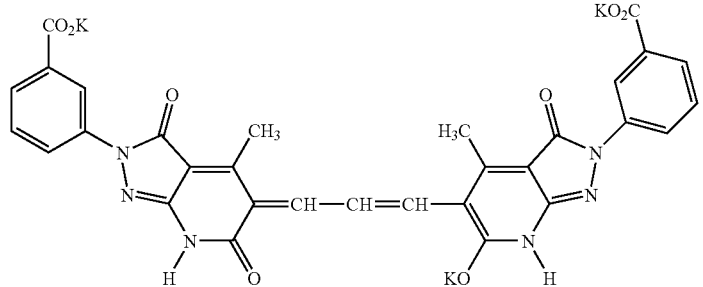
(I-12)
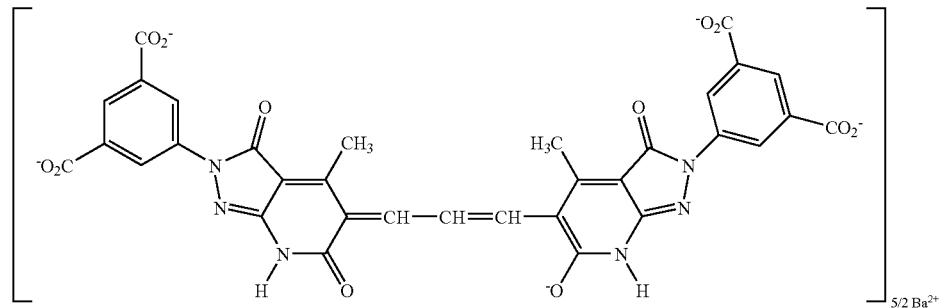
(I-13)
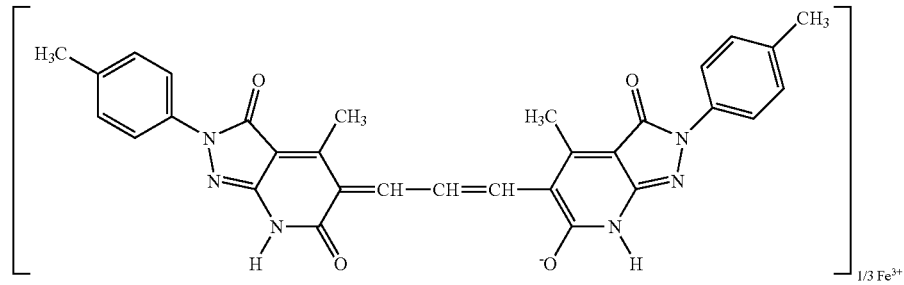
(I-14)
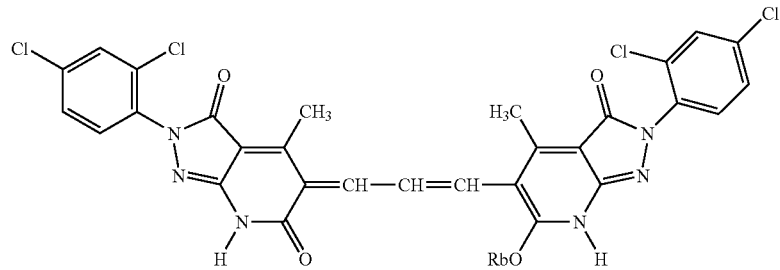
(I-15)
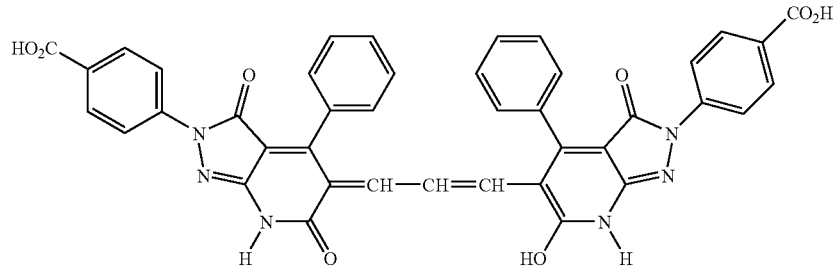
(I-16)

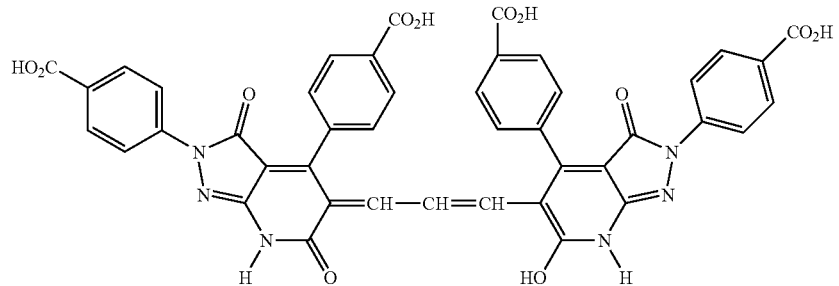
(I-17)
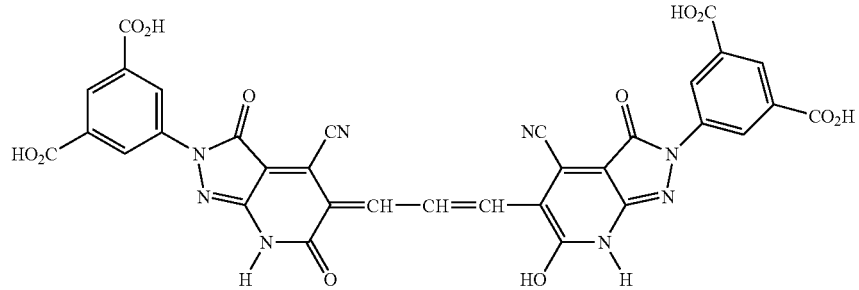
(I-18)
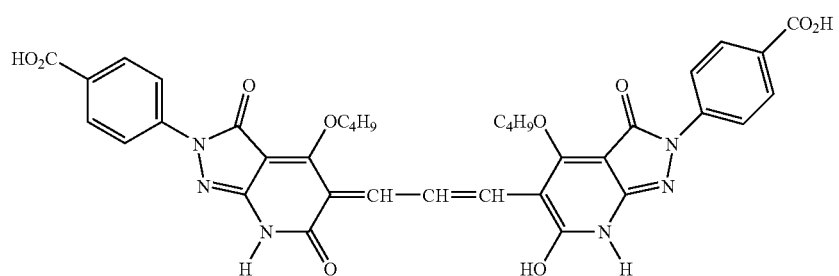
(I-19)
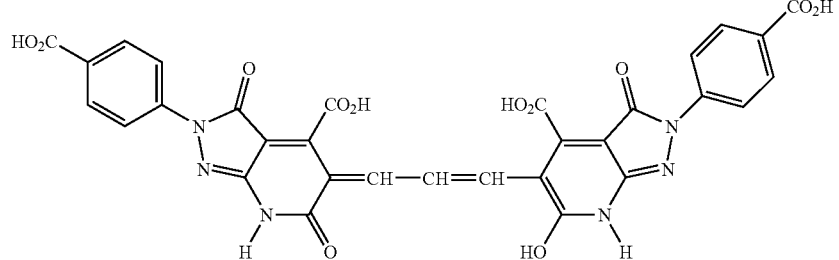
(I-20)
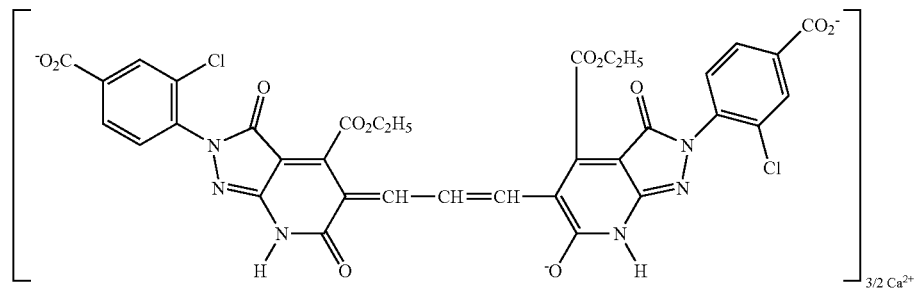
(I-21)

-continued
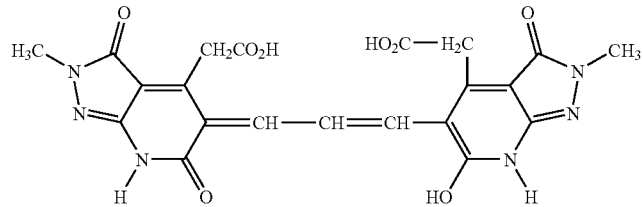
(I-22)
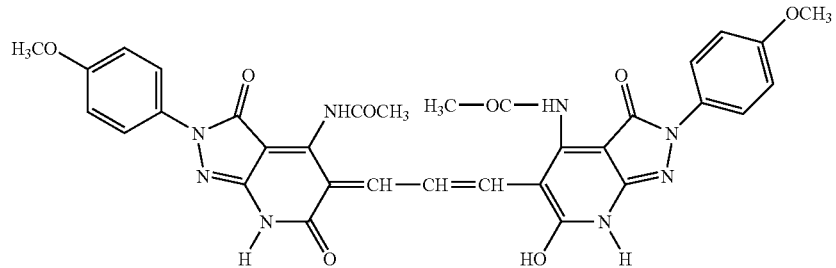
(I-23)
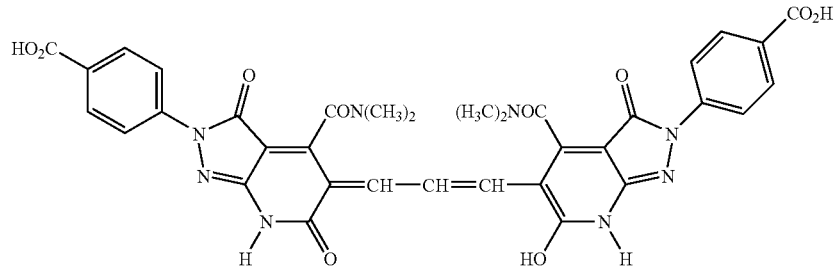
(I-24)
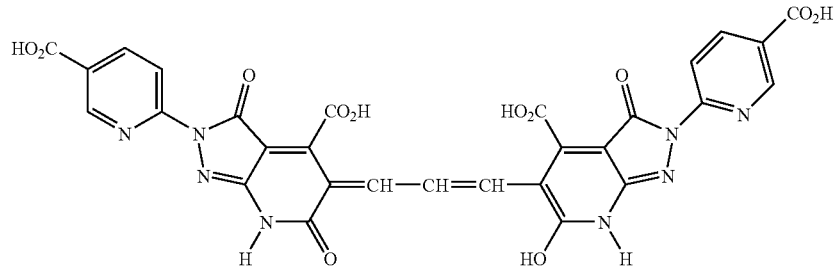
(I-25)
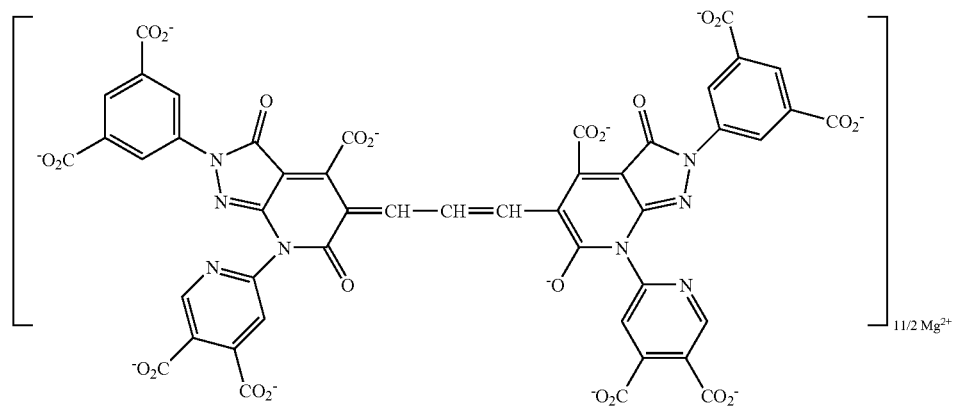
(I-26)

-continued
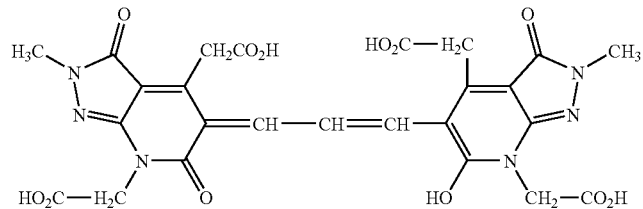
(I-27)
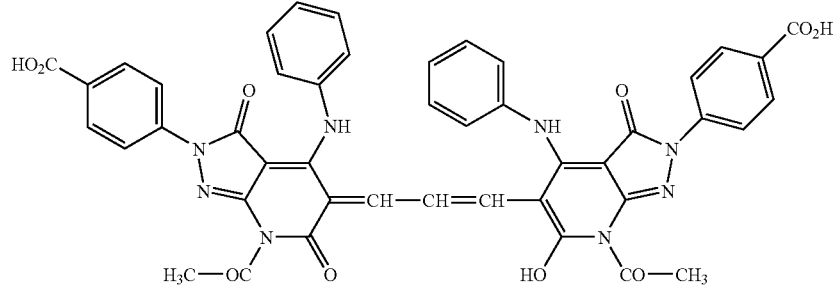
(I-28)
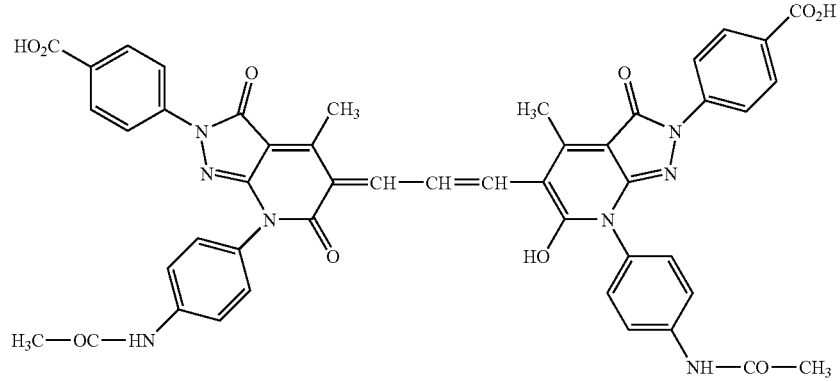
(I-29)
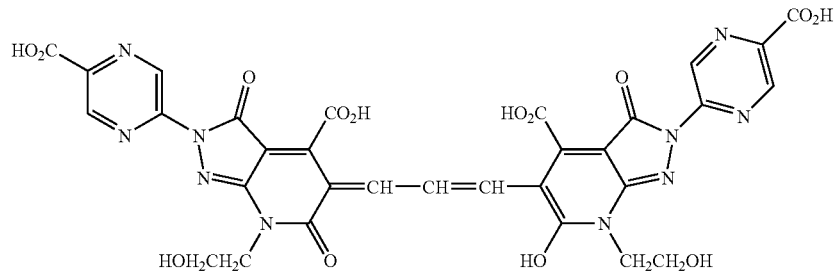
(I-30)
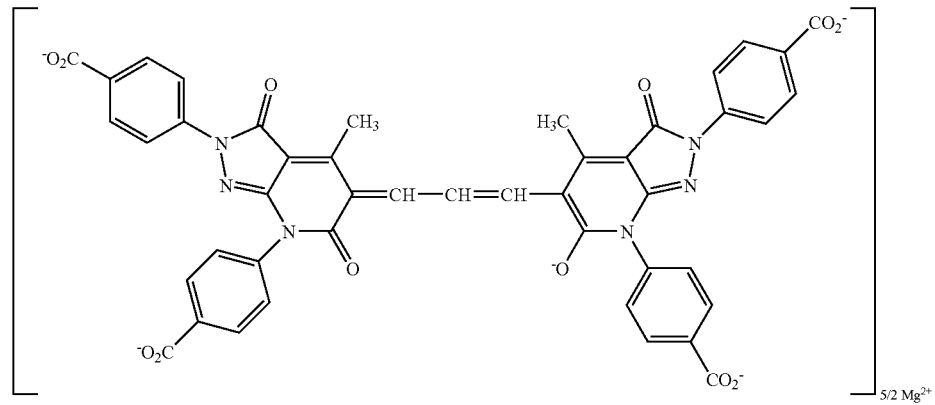
(I-31)

-continued
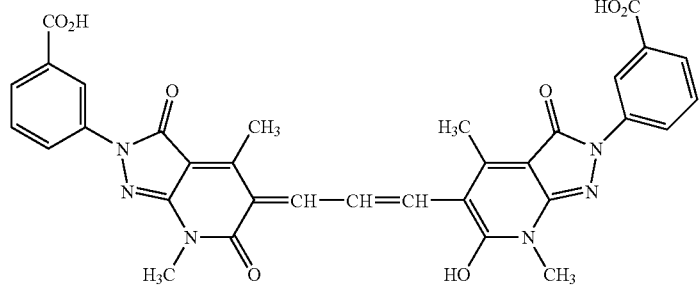
(I-32)
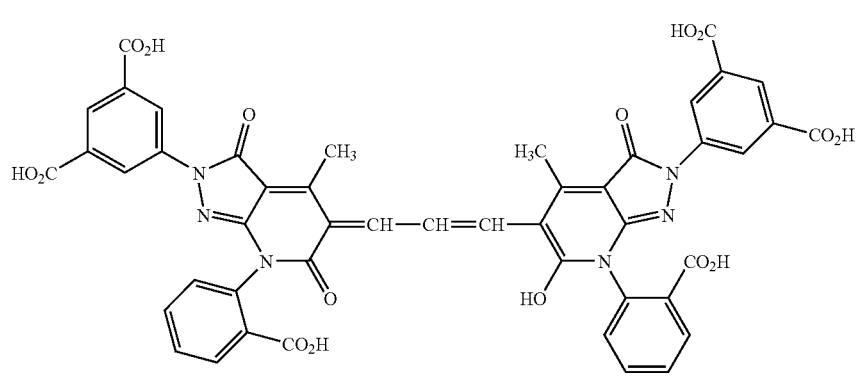
(I-33)
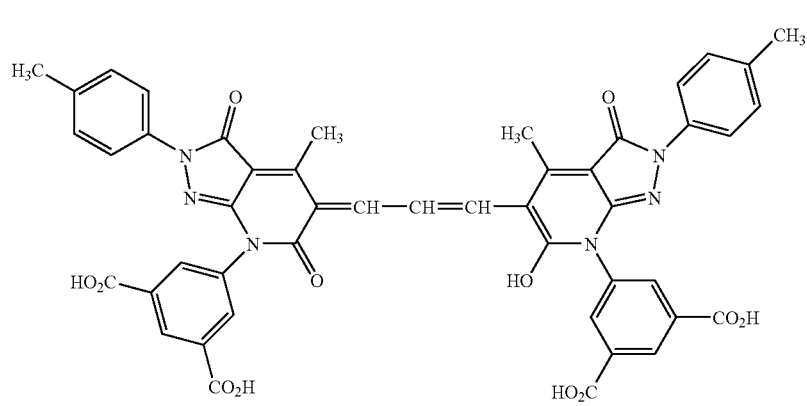
(I-34)
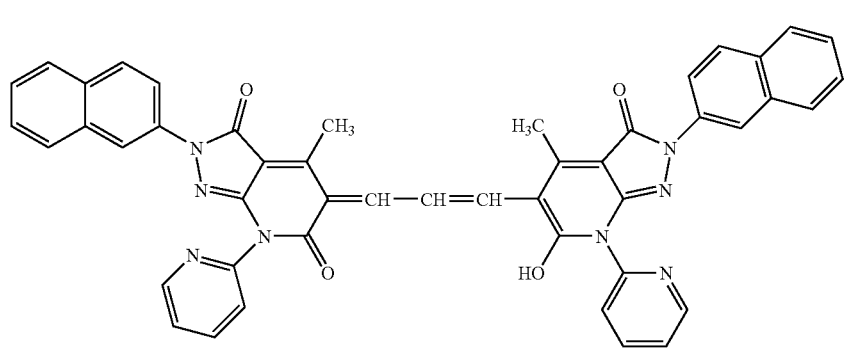
(I-35)

-continued
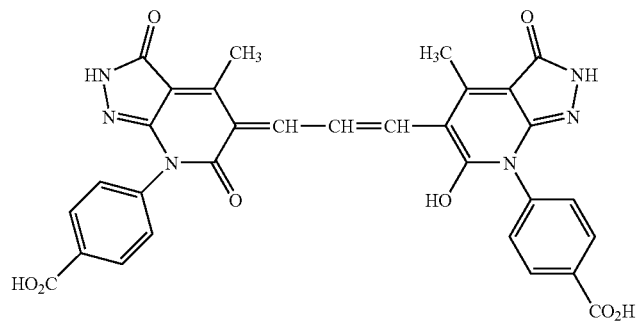
(I-36)
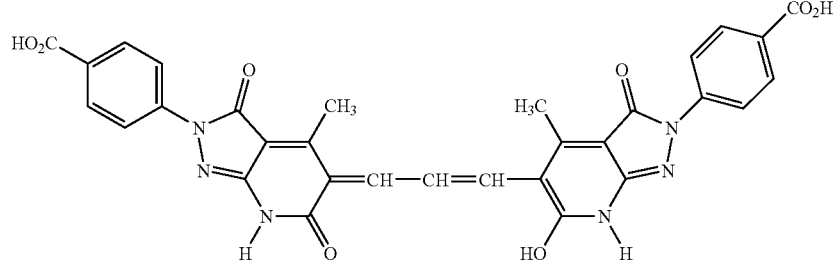
(I-37)
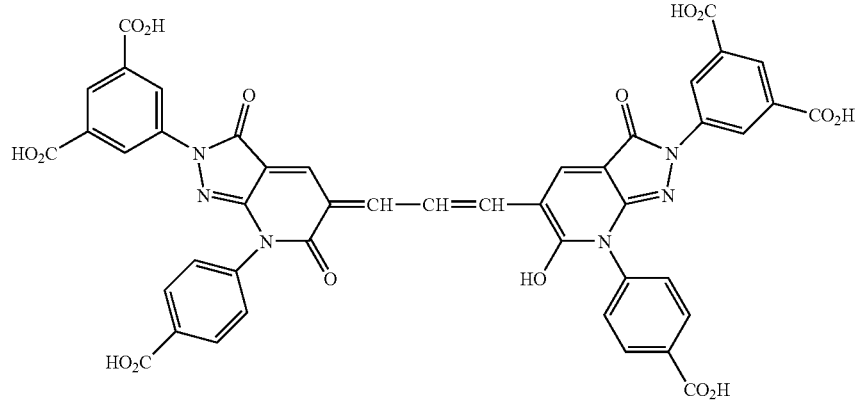
(I-38)
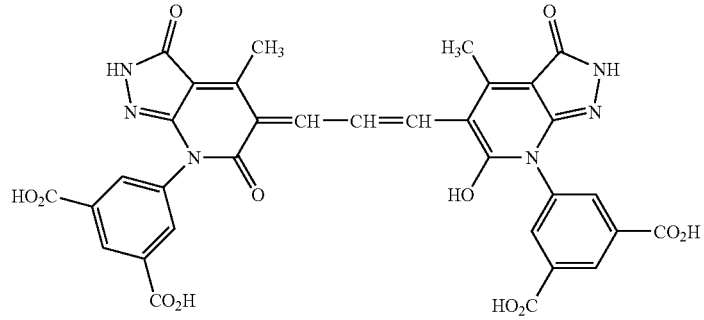
(I-39)
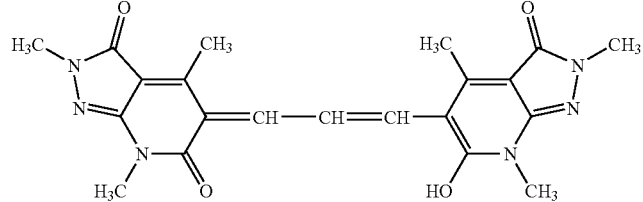
(I-40)

-continued

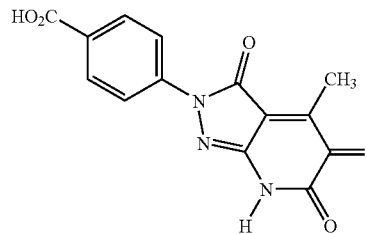

(I-41)

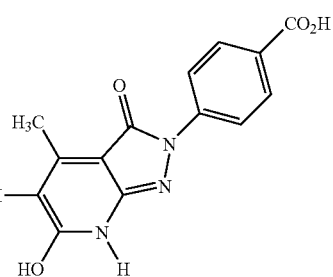

(I-42)

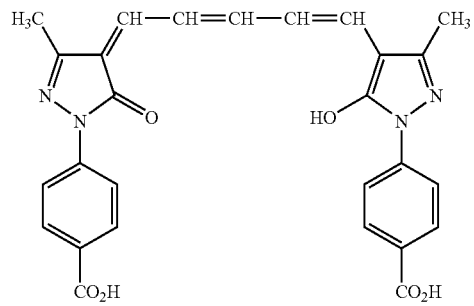

(I-43)

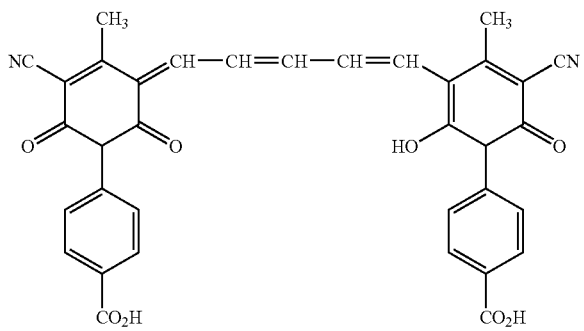

(I-44)

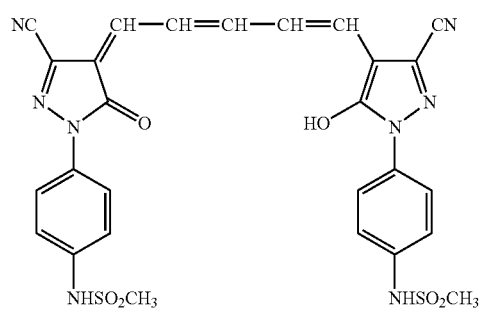

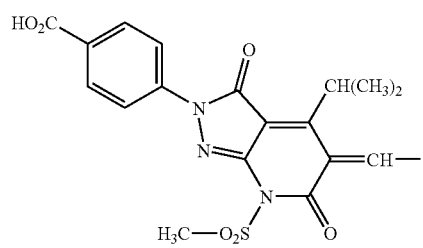

(I-45)

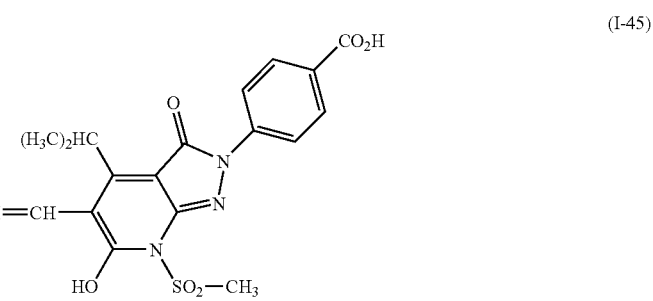

The compound denoted by general formula (I) can be synthesized by, or based upon, the methods described, for example, in U.S. Pat. No. 4,181,225; Japanese Examined Patent Publication (KOKOKU) Showa Nos. 39-22,069,43-3,504,52-38,056,54-38,129, 55-10,059, and 58-35,544; Japanese Unexamined Patent Publication (KOKAI) Showa Nos. 49-99,620,59-16,834, 63-316,853; and Japanese Unexamined Patent Publication (KOKAI) Heisei No. 2-282,244, which are expressly incorporated herein by reference in their entirety.

The black pigment of the present invention can be employed in the form of a powder (crystalline particle) or dispersion, as set forth further below. The particle diameter of the black pigment of the present invention can be adjusted by dry pulverization. Further, the black pigment of the present invention can be added to a suitable solvent (such as water or alcohol) and adjustments can be made mechanically by a known comminution method (such as a ball mill, vibrating ball mill, planetary ball mill, sand mill, colloid mill, jet mill, or roller mill) in the presence of a dispersing agent. A method such as using a dispersing agent to dissolve the black pigment of the present invention in a suitable solvent and adding a poor solvent to cause microcrystals to precipitate out, or controlling the pH, dissolving the black pigment, and subsequently altering the pH to form microcrystals may be employed.

The black pigment of the present invention can be employed as is; mixed with binder and/or other compounds; coated on paper, resin sheet, resin, film, glass, metal sheet, or the like; kneaded; formed into a hard coat; or mixed with a monomer and polymerized; for use in various applications.

Applications include printing and marking materials; paint for construction and transportation equipment; and rubber products such as the tires of delivery equipment. The black pigment of the present invention is highly transparent to near infrared radiation, and thus affords the advantage of permitting clear differentiation from near infrared radiation-absorbing pigments during reading by semiconductor lasers. It also tends not to accumulate heat under direct exposure to sunlight, rendering it suitable to applications such as automobile and building paints and plastic materials. Two or more different kinds of black pigments of the present invention may be employed in combination.

[Black Pigment Dispersion]

The black pigment dispersion of the present invention comprises the black pigment of the present invention and can be obtained, for example, by dispersing the black pigment of the present invention in a suitable solvent.

The solvent employed in the black pigment dispersion of the present invention can be selected based on the application. For example, a water-based paint can be selected for an aqueous paint, and a nonaqueous solvent can be selected for an oil-based paint. Examples of the solvent are: water, amide-based solvents (such as N,N-dimethylformamide, N,N-dimethylacetamide, and 1-methyl-2-pyrrolidone), sulfone-based solvents (such as sulforane), sulfoxide-based solvents (such as dimethylsulfoxide), ether-based solvents (such as dioxane and cyclopentyl methyl ether), ketone-based solvents (such as acetone and methyl ethyl ketone), hydrocarbon-based solvents (such as toluene and xylene), halogen-based solvents (such as tetrachloroethane and chlorobenzene), and alcohol-based solvents (such as methanol, ethanol, isopropanol, 1-butanol, and ethylene glycol), and pyridine based-solvents (such as pyridine, gamma-picoline, 2,6-lutidine), which may be employed singly or mixed for use. The preferred solvents are water, amide-based solvents, sulfone-based solvents, sulfoxide-based solvents, ether-based solvents, ketone-based solvents, and alcohol-based solvents. Solvents of even greater preference are: water, ether-based solvents, ketone-based solvents, and alcohol-based solvents. Solvents of still greater preference are water, methanol, ethanol, and methyl ethyl ketone. Water employed alone is the solvent of greatest preference. These solvents may be added during dispersion, added after dispersion, and removed by distillation.

The transmittance of light having a wavelength of 750 to 1,200 nm of the above dispersion is preferably 60 to 100 percent, more preferably 80 to 100 percent, and further preferably, 90 to 100 percent. Use of the black pigment of the present invention yields a black pigment dispersion having transparency to near infrared radiation falling within the above-stated range. A black dispersion having high transparency to near infrared radiation and exhibiting transmittance within the above-stated range is suited to the various applications set forth above.

The weight ratio of solvent to black pigment during dispersion is preferably 3 to 500 weight parts, more preferably 8 to 200, weight parts further preferably 15 to 100 weight parts, and still more preferably, 20 to 50 weight parts per 1 weight part of black pigment. The content of black pigment in the black pigment dispersion of the present invention is, for example, 0.2 to 30 weight percent, preferably 0.5 to 10 weight percent, and more preferably, 1 to 5 weight percent.

From the perspective of obtaining good dispersion properties, the viscosity of the black pigment dispersion of the present invention is preferably 10 to 100,000 mPa·S, more preferably 30 to 30,000 mPa·S, and further preferably, 50 to 10,000 mPa·S.

The dispersion medium may be conventionally employed glass beads, metal beads, alumina beads, titania beads, zirconia beads, or the like. Ceramic beads such as zirconia beads and titania beads are desirable, with zirconia beads being preferred.

The smaller the diameter of the dispersion medium, the more the irregularities on the surface of the pigment particles can be reduced. Thus, the diameter of the dispersion medium is preferably equal to or less than 2.0 mm, more preferably equal to or less than 1.5 mm, further preferably equal to or less than 1.0 mm, and most preferably, 0.05 to 0.5 mm.

The weight ratio of the dispersion medium to the black pigment during dispersion is preferably 1 to 1,000 weight parts, more preferably 5 to 200 weight parts, further preferably 10 to 150 weight parts, still more preferably 15 to 100 weight parts, and most preferably, 20 to 50 weight parts per 1 weight part of black pigment.

LMJ or LMZ agitator mill, or AMC ultrafine pulverizer, made by Ashizawa Fine Tech (Ltd.); Pure Mill, Nanomill, or Picomill made by Asada Tekko (Ltd.); Super Apex Mill made by Kotobuki Giken Kogyo (Ltd.); SC Mill made by Mitsui Kosan (Ltd.); or the like may be employed as disperser in the dispersion step.

Additives can be added as necessary to the dispersion of the present invention. Examples of additives that are suitable for use are silicone oil; silicone having polar groups; fatty acid-modified silicone; fluorine-containing silicone; fluorine-containing alcohols; fluorine-containing esters; polyolefins; polyglycols; polyphenylether; phenyl phosphonate, benzyl phosphonate groups, phenethyl phosphonate, alpha-methylbenzyl phosphonate, 1-methyl-1-phenethyl phosphonate, diphenylmethyl phosphonate, biphenyl phosphonate, benzylphenyl phosphonate, alpha-cumyl phosphonate, toluoyl phosphonate, xylyl phosphonate, ethylphenyl phosphonate, cumenyl phosphonate, propylphenyl phosphonate, butylphenyl phosphonate, heptylphenyl phosphonate, octylphenyl phosphonate, nonylphenyl phosphonate, and other cyclic aromatic organophosphonic acids and their alkali metal salts; octyl phosphonate, 2-ethylhexyl phosphonate, isooctyl phosphonate, (iso)nonyl phosphonate, (iso)decyl phosphonate, (iso)undecyl phosphonate, (iso)dodecyl phosphate, (iso)hexadecyl phosphate, (iso)octadecyl phosphate, (iso)eicosyl phosphonate, and other alkyl phosphonates and their alkali metal salts; phenyl phosphate, benzyl phosphate, phenethyl phosphate, alpha-methylbenzyl phosphate, 1-methyl-1-phenethyl phosphate, diphenylmethyl phosphate, biphenyl phosphate, benzylphenyl phosphate, alpha-cumyl phosphate, toluoyl phosphate, xylyl phosphate, ethylphenyl phosphate, cumenyl phosphate, propylphenyl phosphate, butylphenyl phosphate, heptylphenyl phosphate, octylphenyl phosphate, nonylphenyl phosphate, and other aromatic phosphoric acid esters and their alkali metal salts; octyl phosphate, 2-ethylhexyl phosphate, isooctyl phosphate, (iso)nonyl phosphate, (iso)decyl phosphate, (iso)undecyl phosphate, (iso)dodecyl phosphate, (iso)hexadecyl phosphate, (iso)octadecyl phosphate, (iso)eicosyl phosphate, and other alkyl phosphoric acid esters and their alkali metal salts; alkyl sulfonic acid esters and their alkali metal salts; fluorine-containing alkyl sulfturic acid esters and their alkali metal salts; lauric acid, myristic acid, palmitic acid, stearic acid, behenic acid, butyl stearate, oleic acid, linolic acid, linoleic acid, elaidic acid, ercaic acid, and other optionally branched monobasic fatty acids containing unsaturated bonds and having 10 to 24 carbon atoms, and their metal salts; monofatty acid esters, difatty acid esters, and polyfatty acid esters comprised of an optionally branched monobasic fatty acid having 10 to 24 carbon atoms, optionally having one or more unsaturated bonds, such as butyl stearate, octyl stearate, amyl stearate, isooctyl stearate, octyl myristate, butyl laurate, butoxyethyl stearate, anhydrosorbitan monostearate, anhydrosorbitan distearate, and anhydrosorbitan tristearate, and at least one member selected from the group consisting of optionally branched monohydric to hexahydric alcohols containing 2 to 22 carbon atoms, optionally containing one or more unsaturated bonds, optionally branched alkoxy alcohols containing 12 to 22 carbon atoms, optionally containing one or more unsaturated bonds, and monoalkyl ethers of alkylene oxide polymerized products; fatty acid amides having 2 to 22 carbon atoms; and fatty acid amines having 8 to 22 carbon atoms. In addition to the above-described hydrocarbon groups, an additive having an alkyl group, aryl group, aralkyl group, or the like substituted with a group other than a hydrocarbon group, such as a nitro group, F, Cl, Br, or a halogen-containing hydrocarbon such as $CF_3$, $CCl_3$, or $CBr_3$, may also be employed. Nonionic surfactants such as alkylene oxide-based, glycerin-based, and glycidol-based surfactants, as well as alkylphenolethylene oxide adducts; cationic surfactants cyclic amines, ester amides, quaternary ammonium salts, hydantoin derivatives, heterocyclic compounds, phosphonium, and sulfoniums; anionic surfactants containing acidic groups such as carboxylic acid, sulfonic acid, or sulfuric acid esters; and amphoteric surfactants such as amino acids, aminosulfonic acids, sulfuric and phosphoric esters of aminoalcohols, and alkylbetaine-type compounds may be employed. These surfactants are described in detail in *A Guide to Surfactants* (published by Sangyo Tosho Co.). These compounds need not necessarily be pure, and may contain impurities in the form of isomers, unreacted substances, side reaction products, decomposition products, oxides, and the like in addition to the main component. The content of these impurities is preferably equal to or less than 30 weight percent, more preferably equal to or less than 10 weight percent. These additives may be employed singly or in combinations of two or more.

Among these additives, nonionic surfactants, anionic surfactants, and cationic surfactants are preferred. Nonionic surfactants and anionic surfactants are of greater preference. Nonionic surfactants are of even greater preference. Polyalkylene glycol-based surfactants are of still greater preference. Polyethylene glycol-based surfactants are of yet greater preference. And polyethylene glycol surfactants having an average molecular weight of 3,000 to 30,000 are of the greatest preference.

The above additives may be added during the dispersion step, or after dispersion. Addition during the dispersion step is most preferred.

The quantity of additive in the above dispersion is preferably equal to or less than 20 weight percent, more preferably 0.01 to 15 weight percent, further preferably 0.05 to 12 weight percent, even more preferably 0.1 to 10 weight percent, and still more preferably, 1 to 8 weight percent.

[Black Resin Composition]

The black resin composition of the present invention comprises the black pigment of the present invention and a resin component.

Examples of the resin component are: ABS resin, polyethylene resin, polypropylene resin, polyvinyl chloride resin, polycarbonate resin, polystyrene resin, polyacrylonitrile resin, methacrylonitrile resin, polymethyl methacrylate resin, polyester resin, polyisoprene resin, polyvinylidene chloride resin, polymethacrylate resin, polyethacrylate resin, poly(2-ethylhexyl acrylate) resin, polyethyl methacrylate resin, polybutyl methacrylate resin, polyethylene glycol dimethacrylate resin, polydivinyl benzene resin, polyvinyl toluene resin, poly(alpha-methylstyrene) resin, polyvinyl acetate resin, polyvinyl propionate resin, polyvinyl cinnamate resin, poly(N-tert-butylacrylamide) resin, poly(N-cyclohexylacrylamide) resin, and polymethacrylamide resin. Preferred resins are polypropylene resin, polyvinyl chloride resin, polycarbonate resin, polystyrene resin, polyacrylonitrile resin, methacrylonitrile resin, polymethyl methacrylate resin, polyester resin, polyisoprene resin, polymethacrylate resin, polyethacrylate resin, polyethyl methacrylate resin, polybutyl methacrylate resin, polyvinyl toluene resin, poly(alpha-methylstyrene) resin, poly(N-cyclohexylacrylamide) resin, and polymethacrylamide resin.

The black resin composition of the present invention can be obtained by kneading the black pigment of the present invention with the resin component with heating, or, for example, by adding the resin to the black pigment dispersion of the present invention, melting the mixture by heating, working the mixture to achieve a fine consistency, and forming a thin film or molding, or solidifying the mixture as is.

The black resin composition of the present invention can be, for example, in the form of a film, plate, powder, or solid, and can be formed into a final form by a forming method based on the application.

The black resin composition of the present invention preferably has a transmittance of light having a wavelength of 750 to 1,200 nm in a range of 60 to 100 percent, more preferably 80 to 100 percent, further preferably 90 to 100 percent. Use of the black pigment of the present invention permits the obtaining of a black resin composition having near infrared radiation transparency in the above-stated range. The black resin composition having high transparency to near infrared radiation and exhibiting transmittance over the above-stated range is suited to the various applications stated above.

The content of black pigment in the black resin composition of the present invention is, for example, 0.2 to 40 weight percent, preferably 0.3 to 30 weight percent, more preferably 0.5 to 20 weight percent, and still more preferably, 1.0 to 10 weight percent.

In addition to the above-stated components, the black resin composition of the present invention also desirably comprises ultraviolet radiation-absorbing agents such as benzotriazoles, benzophenones, and coumarins; radical-trapping agents and antioxidants such as phenols and amines; and other storage-enhancing agents.

EXAMPLES

The present invention will be described in detail below based on examples. However, the present invention is not limited to the examples.

Example 1

Preparation of Black Pigment Dispersion

To 10.0 g of exemplified compound (I-1) and 2.0 g of a polyethyleneoxide-based compound (Pluronic F88 made by BASF Corp.) was added 88 mL of water. The mixture was placed in a batch-type sand mill, 300 g of zirconia beads (1 mm diameter) were added, and the mixture was dispersion processed for 5 minutes at 3,000 rpm. Subsequently, the contents were recovered and the beads were filtered out to obtain the targeted dispersion (dispersion 101).

Evaluation of Physical Properties of the Dispersion (1) Mean Particle Diameter of the Pigment The mean particle diameter of the pigment comprised in the dispersion obtained was 0.58 micrometer as measured with an LA-920A Laser Diffraction and Scattering Type Particle Size Distribution Measuring Device made by Horiba, Ltd.

(2) Viscosity Measurement

The viscosity of the dispersion obtained was 900 mPa·S as measured at 25° C. with an RE-80R Model E Viscosity System made by Toki Sangyo.

(3) Near Infrared Radiation Transmittance

The optical transmittance of the dispersion obtained was greater than 73 percent at 750 to 1,200 nm as measured with a U-4100 Spectrophotometer made by Hitachi High Technologies (Ltd.).

Example 2

Dispersions 102 to 112 were obtained by the same method as in Example 1, with the exception that the pigment, additives, and dispersion conditions employed were altered as indicated in Table 1. The physical properties of each of the dispersions obtained were evaluated in the same manner as in Example 1. As indicated in Table 1, the dispersions obtained all exhibited high near infrared radiation transparency. Further, good dispersion properties were confirmed in all cases based on the results of viscosity and particle size measurement.

Example 3

When the dispersions of Examples 1 and 2 were respectively coated on paper, they were visually observed to have adequate blackness.

Example 4

The dispersions obtained in Examples 1 and 2 were respectively irradiated with Xe for two minutes at 170,000 lux (Merry-go-round Type Xenon Light-Resistance Tester III, 500 W model, made by Eagle Engineering Corp.). As shown in Table 2, a greater inhibiting effect on temperature increase was observed than carbon black.

TABLE 2

| Dispersion | Surface temperature (° C.) |
|---|---|
| 101 | 47 |
| 104 | 48 |
| 106 | 46 |
| 107 | 46 |
| 108 | 49 |
| 109 | 46 |
| 110 | 48 |
| 111 | 47 |
| 112 | 47 |
| Comparative Example 1 | 59 |

Comparative Example 1: Dispersion of carbon black (made by Wako Pure Chemical Industries, Ltd., activated carbon, powder)

TABLE 1

| | | Additive | | Beads | | Results | | |
| | | | | | | | | Minimum |
| Dispersion | Pigment (Exemplified compound) | Type | Content (per wt % of pigment) | Type | Content (per wt % of pigment) | Particle diameter (micrometer) | Viscosity (mPA·s) | transmittance at 750-1200 nm |
|---|---|---|---|---|---|---|---|---|
| 102 | (I-1) | Pluronic F88 | 20 | Zirconia (0.3 mm) | 30 times | 0.31 | 1020 | 82% |
| 103 | (I-1) | Pluronic F88 | 10 | Zirconia (0.5 mm) | 30 times | 0.55 | 1300 | 68% |
| 104 | (I-1) | PEG-OP | 10 | Zirconia (0.3 mm) | 50 times | 0.21 | 920 | 80% |
| 105 | (I-1) | PEG-PPG | 10 | Zirconia (0.3 mm) | 50 times | 0.44 | 880 | 70% |
| 106 | (I-3) | PEG-OP | 20 | Zirconia (0.3 mm) | 30 times | 0.39 | 1360 | 67% |
| 107 | (I-4) | PEG-OP | 20 | Zirconia (0.3 mm) | 30 times | 0.30 | 960 | 72% |
| 108 | (I-7) | PEG-OP | 20 | Zirconia (0.3 mm) | 30 times | 0.44 | 940 | 71% |
| 109 | (I-8) | PEG-OP | 20 | Zirconia (0.3 mm) | 30 times | 0.49 | 930 | 74% |
| 110 | (I-18) | PEG-OP | 20 | Zirconia (0.3 mm) | 30 times | 0.41 | 890 | 77% |
| 111 | (I-24) | PEG-OP | 20 | Zirconia (0.3 mm) | 30 times | 0.39 | 990 | 70% |
| 112 | (I-25) | PEG-OP | 20 | Zirconia (0.3 mm) | 30 times | 0.27 | 1120 | 65% |

PEG-OP: Polyethyleneglycol mono-4-octylphenylether
PEG-PPG: Polyethyleneglycol-polypropyleneglyocol (average molecular weight: 11,800)

Example 5

A 100 mL quantity of chloroform was added to 0.7 g of micropowder obtained by filtering and drying the dispersions shown in Table 3, and the components were stirred for 15 minutes at 40° C. The mixtures obtained were coated onto glass sheets and dried by air blowing at room temperature to prepare sample films.

Film Evaluation (1) Transparency to Near Infrared Radiation

The minimum transmittance at 750 to 1,200 nm of the sample films obtained in Example 5 was measured with a U-4100 Spectrophotometer made by Hitachi High Technologies (Ltd.); the results are given in Table 3.

(2) Evaluation of Thermal Stability

When the sample films obtained in Example 5 were stored for three days at 60° C., visual observation of the sample obtained using carbon black in Comparative Example 2 revealed roughness on the surface of the film. However, samples 201 to 212 were all smooth, without major change in surface condition.

TABLE 3

| Sample | Dispersion | Minimum transmittance at 750 to 1200 nm |
|---|---|---|
| 201 | 101 | 70% |
| 202 | 102 | 77% |
| 203 | 103 | 66% |
| 204 | 104 | 74% |
| 205 | 105 | 70% |
| 206 | 106 | 65% |
| 207 | 107 | 68% |
| 208 | 108 | 71% |
| 209 | 109 | 70% |
| 210 | 110 | 72% |
| 211 | 111 | 65% |
| 212 | 112 | 63% |
| Comparative Example 2 | | 1% |

Comparative Example 2: Dispersion of carbon black (made by Wako Pure Chemical Industries, Ltd., activated carbon, powder) was employed.

The black pigment of the present invention is suitable for use in various applications in which high near infrared radiation transmittance is required.

Although the present invention has been described in considerable detail with regard to certain versions thereof, other versions are possible, and alterations, permutations and equivalents of the version shown will become apparent to those skilled in the art upon a reading of the specification and study of the drawings. Also, the various features of the versions herein can be combined in various ways to provide additional versions of the present invention. Furthermore, certain terminology has been used for the purposes of descriptive clarity, and not to limit the present invention. Therefore, any appended claims should not be limited to the description of the preferred versions contained herein and should include all such alterations, permutations, and equivalents as fall within the true spirit and scope of the present invention.

Having now fully described this invention, it will be understood to those of ordinary skill in the art that the methods of the present invention can be carried out with a wide and equivalent range of conditions, formulations, and other parameters without departing from the scope of the invention or any embodiments thereof.

All patents and publications cited herein are hereby fully incorporated by reference in their entirety. The citation of any publication is for its disclosure prior to the filing date and should not be construed as an admission that such publication is prior art or that the present invention is not entitled to antedate such publication by virtue of prior invention.

What is claimed is:

1. A black pigment consisting of an oxonol compound having a mean particle diameter ranging from 0.01 to 10.0 micrometers,
   wherein said compound is a compound denoted by general formula (I)

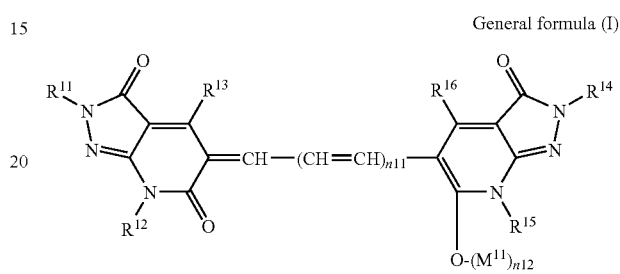

General formula (I)

wherein,
$R^{11}$ and $R^{14}$ each independently denotes a hydrogen atom, an aliphatic group, an aromatic group, or a heterocyclic group bonded through a carbon atom;
$R^{12}$ and $R^{15}$ each independently denotes a hydrogen atom, an aliphatic group, an aromatic group, a heterocyclic group bonded through a carbon atom, $-COR^{17}$, or $-SO_2R^{17}$, $R^{17}$ denotes an aliphatic group, an aromatic group, or a heterocyclic group bonded through a carbon atom;
$R^{13}$ and $R^{16}$ each independently denotes a hydrogen atom, an aliphatic group, an aromatic group, a heterocyclic group, a cyano group, $-CO_2R^{19}$, $-OR^{19}$, $-NR^{19}R^{20}$, $-N(R^{19})COR^{18}$, $-CONR^{18}R^{19}$, or $-N(R^{19})CONR^{20}R^{21}$, $R^{18}$ denotes an aliphatic group, an aromatic group, or a heterocyclic group bonded through a carbon atom, $R^{19}$, $R^{20}$, and $R^{21}$ each independently denote a hydrogen atom, an aliphatic group, an aromatic group, or a heterocyclic group bonded through a carbon atom;
n11 denotes 1 or 2;
$M^{11}$ denotes a calcium ion or a magnesium ion; and
n12 denotes an inverse number of the valence of $M^{11}$, and
wherein a black pigment dispersion comprising the black pigment has a transmittance of light having a wavelength of 750 to 1,200 nm in a range of 60 to 100 percent.

2. A black pigment dispersion comprising the black pigment of claim 1.

3. The black pigment dispersion of claim 2, which comprises said black pigment in an amount of 0.2 to 30 weight percent.

4. A black resin composition comprising the black pigment of claim 1 and a resin component.

5. The black resin composition of claim 4, which comprises said black pigment in an amount of 0.2 to 40 weight percent.

6. The black resin composition of claim 4, which has a transmittance of light having a wavelength of 750 to 1,200 nm in a range of 60 to 100 percent.

* * * * *